US012751627B2

(12) United States Patent
Puppels et al.

(10) Patent No.: US 12,751,627 B2
(45) Date of Patent: Oct. 6, 2026

(54) FIBER OPTIC NEEDLE PROBE

(71) Applicant: ERASMUS UNIVERSITY MEDICAL CENTER ROTTERDAM, Rotterdam (NL)

(72) Inventors: Gerwin Jan Puppels, Schiedam (NL); Tom Christian Bakker Schut, Zoetermeer (NL); Senada Koljenovic, Schiedam (NL); Martin Van Der Wolf, Nieuw-Beijerland (NL); Alexey Bocharnikov, Berlin (DE); Iskander Usenov, Geislingen an der Steige (DE); Viacheslav Artyushenko, Zeuthen (DE); Elisa Maria Barroso, Rotterdam (NL); Yassine Aaboubout, The Hague (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 61 days.

(21) Appl. No.: 18/681,739

(22) PCT Filed: Aug. 10, 2021

(86) PCT No.: PCT/NL2021/050503
§ 371 (c)(1),
(2) Date: Feb. 6, 2024

(87) PCT Pub. No.: WO2023/018327
PCT Pub. Date: Feb. 16, 2023

(65) Prior Publication Data

US 2025/0134386 A1 May 1, 2025

(51) Int. Cl.
*A61B 5/00* (2006.01)
*G02B 6/36* (2006.01)

(52) U.S. Cl.
CPC .......... *A61B 5/0084* (2013.01); *A61B 5/0075* (2013.01); *A61B 5/6848* (2013.01);
(Continued)

(58) Field of Classification Search
CPC ... A61B 5/0084; A61B 5/0075; A61B 5/6848; A61B 2562/0233; A61B 2562/12;
(Continued)

(56) References Cited

U.S. PATENT DOCUMENTS 4,551,129 A * 11/1985 Coleman .............. A61B 3/0008 600/249
6,564,087 B1 * 5/2003 Pitris ......................... G01J 1/00 600/478
(Continued)

FOREIGN PATENT DOCUMENTS

WO WO-2014162289 A1 * 10/2014 ........... A61B 5/0084

OTHER PUBLICATIONS

Engineering Toolbox (https://www.engineeringtoolbox.com/young-modulus-d_417.html; retrieved Mar. 20, 2026).*
(Continued)

*Primary Examiner* — Carolyn A Pehlke
(74) *Attorney, Agent, or Firm* — Leydig, Voit & Mayer, Ltd.

(57) ABSTRACT

A fiber optic needle probe is described that includes a length of optical fiber inside a hollow needle for supporting the optical fiber along its length. A distal end of the optical fiber is formed by a formed convex tip protruding beyond a distal end of the hollow needle. The distal end of the optical fiber is formed by a formed conical tip with a cone angle less than hundred degrees. The shape of the convex tip formed at the distal end of the optical fiber is found particularly suitable for repeated insertion into a tissue with minimal tendency of tissue residue sticking to the tip.

13 Claims, 5 Drawing Sheets

(52) U.S. Cl.
CPC ... *A61B 2562/0233* (2013.01); *A61B 2562/12* (2013.01); *G02B 6/3624* (2013.01)

(58) Field of Classification Search
CPC .. G02B 3/0025; G02B 6/3624; G02B 6/3628; G02B 2006/12197
See application file for complete search history.

(56) References Cited

U.S. PATENT DOCUMENTS

| | | | | |
|---|---|---|---|---|
| 6,916,329 | B1 * | 7/2005 | Zhao | A61N 1/0502<br>606/189 |
| 8,277,411 | B2 * | 10/2012 | Gellman | A61B 1/015<br>604/131 |
| 2001/0012429 | A1 | 8/2001 | Wach et al. | |
| 2008/0051770 | A1 | 2/2008 | Scheller et al. | |
| 2011/0229841 | A1 * | 9/2011 | Hamada | A61C 1/0046<br>433/29 |
| 2013/0079598 | A1 | 3/2013 | Auld et al. | |
| 2016/0155363 | A1 * | 6/2016 | Rios | G09B 5/00<br>434/262 |
| 2018/0317818 | A1 * | 11/2018 | Puppels | G01N 21/4795 |
| 2020/0138296 | A1 * | 5/2020 | Pisanello | A61B 5/0075 |

OTHER PUBLICATIONS

European Patent Office, International Search Report in corresponding International Application No. PCT/NL2021/050503 dated May 6, 2022.

* cited by examiner

FIBER OPTIC NEEDLE PROBE

CROSS-REFERENCE TO RELATED APPLICATIONS

This patent application is a U.S. National Phase of PCT International Application No. PCT/NL2021/050503, filed Aug. 10, 2021, which is expressly incorporated by reference in its entirety, including any references contained therein.

TECHNICAL FIELD AND BACKGROUND

The present disclosure relates to a fiber optic needle probe, e.g., for the analysis of tissue composition by light interaction.

A major factor in the success of tumor surgery is the ability of a surgeon to exactly determine a border between the tumor and surrounding healthy tissue, and then resect the tumor, including a so-called safe surgical margin. Typically, the surgeon roughly knows the location of the tumor, e.g., from preoperative CT/MRI images but, during resection, has to rely on visual inspection and palpation. This can lead to inadequate resections in which the tumor is not completely removed or not removed with an adequate safe surgical margin, associated with a higher risk of tumor recurrence, the need for adjuvant therapy, and reduced survival. One way of measuring tissue composition is by measuring interaction with light, e.g., spectral analysis. To measure a spectrum at a specific location inside the tissue, light can be transported to and from the location via a fiber optic needle probe. For example, Raman spectroscopy is an optical spectroscopic technique that can be used for intraoperative assessment of the tumor border for various types of cancer WO 2017/126955 A1 describes an instrument with a fiber optic needle probe. The probe comprises a needle having a needle tip formed to penetrate a tissue surface and an optical waveguide, e.g., optical fiber, arranged to transmit light through the needle. Localized concentrations of an analyte are measured at a plurality of spaced apart locations around a controlled depth below the tissue surface. Spatial variance of the analyte is calculated based on the measured analyte concentrations. The procedure is repeated while varying the controlled depth to obtain the spatial variance as a function of depth. Tissue at a particular depth may be evaluated as tumor tissue when the spatial variance is below the threshold. For example, a section distance is calculated between the tissue surface and a depth where the measured spatial variance crosses a predetermined threshold variance.

WO 2014/162289 A1 describes another fiber optic needle probe, in particular a medical needle which comprises an elongate tube and at least one optical fiber, e.g. two fibers, arranged within the elongate tube, for making optical measurements at the distal end of the needle. The optical fibers(s) has a beveled distal end surface, wherein a plane touching the beveled distal end surface and a longitudinal extension axis of the optical fiber forms a bevel angle which is 30°-35°. According to this prior art, such needle is advantageous for providing a medical needle which is reliable and long term stable, can be manufactured in low cost using known optical fiber materials, thus allowing it to form part of disposable medical kits. Still, the bevel angle of 30°-35° provides a needle which is easy to insert and which provides a low tendency to cause tissue sticking. Especially, the elongate tube and the optical fiber end(s) have the same beveled angle within the range 30°-35°, thus allowing a smooth front surface of the needle.

There is a need for a further improved fiber optic needle probe which can be easily and repeatedly inserted into a tissue to reach a controlled location, providing reliable measurement without requiring a very specific bevel angle.

SUMMARY

Aspects of the present disclosure provide a fiber optic needle probe. The probe comprises a hollow needle or tube. The probe further comprises a length of optical fiber inside the hollow needle for supporting the length of the optical fiber. In this way the optical fiber can be protected and accurately guided, e.g. without inadvertent bending which could affect the accuracy of the measurement location. Advantageously, a distal end of the optical fiber can be formed into a (sharp) convex tip, e.g. by means of mechanical, chemical or laser processing. For example, the tip can be polished or otherwise processed to reach a relatively high smoothness. The convex tip of the fiber protrudes beyond the distal end of the hollow needle. By providing the optical fiber with a convex, preferably conical, tip which protrudes beyond the supporting end of the surrounding needle, the reliability of measured tissue spectra can be surprisingly improved. In particular, the convex/sharpened shape of the protruding fiber optic tip can reduce the problem of interfering signal background, caused by fouling of the fiber optic probe tip through the accumulation of tissue (components), thereby enabling repeated use of the fiber optic probe.

Without being bound by theory, the inventors find that when a fiber optic needle probe is inserted in tissue and/or retracted, residual tissue components may accumulate and stick to the fiber optic probe surface. It is particularly found that the tissue material attaches predominantly to irregularities, microcavities, and other roughnesses in the probe surface. Such residual material may then be in the path of light that is guided to the tissue and/or in the path of the light being collected from the tissue. This may thereby affect results, in particular of subsequent measurements with the said probe, and thereby the reliability of the tissue analysis, and/or may make it impossible to continue to use said probe without first cleaning the probe surface.

The inventors find that in a fiber optic needle probe, fouling tissue on the distal end of the probe predominantly tends to accumulate at the borders between different material, such as the interface between the optical fiber cladding and coating, and/or the interface between the coating and glue, and/or the interface between the glue and surrounding needle/tube. By providing the optical fiber with a sharp tip that protrudes beyond the end of the needle, fouling tissue tends to slide off the tip of the fiber and move to the surrounding perimeter, where it is typically beyond the field of view of the fiber and therefore does not affect the measurement. Most preferably, the tip is formed into a conical form centered on the inner core. In this way, the core can protrude from the surrounding cladding, the cladding can protrude from the surrounding coating, and the coating can protrude from the surrounding needle/tube. Accordingly, the interfaces where fouling tissue may stick can be disposed behind the protruding core/cladding of the fiber.

Furthermore, from experiments described herein, the inventors find that even in occasions when tissue does accumulate at the end of the conic shaped optical fiber core, immediately upon retraction of the needle probe from the tissue, said tissue accumulation tends to be removed when the needle probe is re-inserted in tissue, and therefore, does not affect subsequent optical measurements for tissue analysis. This makes the conical or near-conical fiber optic needle probe especially suited for use in applications in which the needle probe needs to be used multiple times, e.g. to enable tissue analysis or tissue classification at multiple locations in a tissue.

BRIEF DESCRIPTION OF DRAWINGS

These and other features, aspects, and advantages of the apparatus, systems, and methods of the present disclosure will become better understood from the following description, appended claims, and accompanying drawing wherein:

DESCRIPTION OF EMBODIMENTS

Figure 1A:
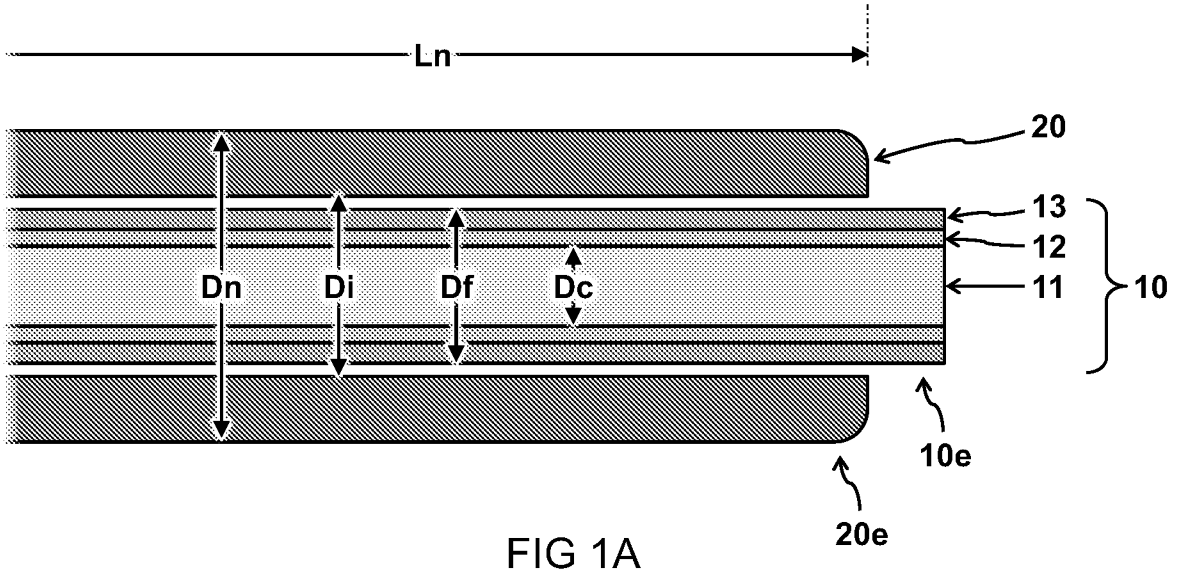
FIGS. 1A-1C illustrate manufacturing a fiber optic needle probe.

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

When contamination occurs on the tip of a fiber-optic needle probe, in a manner that the contamination is in the path of light guided to the tissue, and/or in the path of the light returned by the tissue into the fiber-optic needle probe, this may affect the result of the intended tissue characterization. First, the contamination is illuminated by the light guided by the fiber-optic needle probe to the tissue and may return light into the fiber-optic needle probe, which is characteristic for the contamination but not for the tissue of interest at the distal end of the probe. Second, the contamination may lead to scattering (or absorption) of the light guided by the fiber-optic needle probe in directions different from the direction of the said light in the absence of the contamination. Similarly, the contamination may lead to scattering (or absorption) of the light returned by the illuminated tissue in a manner that it will not be captured by and guided away by the fiber-optic needle probe in the same way as in the absence of the contamination. This may affect the effective measurement volume and/or the signal intensity in an uncontrolled way. In this way, the needle probe tip contamination may negatively affect the analysis of tissue present at a certain depth under the tissue surface, either by reduced signal intensity or/and by receiving the signal from the contamination itself, or by receiving the signal from a tissue volume that is different from the tissue volume from which signal would have been received in the absence of the contamination. This is particularly relevant in the field of oncology, where the accurate determination of resection margin can affect the success of tumor surgery.

Preferably, the optical fiber as described herein is encapsulated in a hard and rigid material, e.g. by inserting and fixating the optical fiber in the lumen of a metal tubing to form a needle. This may facilitate tissue analysis at a certain distance from the tissue surface, and prevent inadvertent bending of the fiber. To facilitate puncturing of the tissue surface and further insertion in tissue, the distal end of the optical fiber can be formed in a suitable shape, e.g. in the shape of a hypodermic needle. More preferably, the optical fiber is fixed, e.g. glued inside the surrounding needle. Most preferably, the conically formed fiber-optic needle probe for tissue analysis is comprised of a single optical fiber glued into the lumen of a hollow tube made of a polishable material, preferably metal. The distal end can be formed, e.g., into a conical shape and can be inserted at a certain distance into the tissue, through a tissue surface, to enable the application of an optical technique for analysis or classification of said tissue at the said distance from the said tissue surface.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1B:
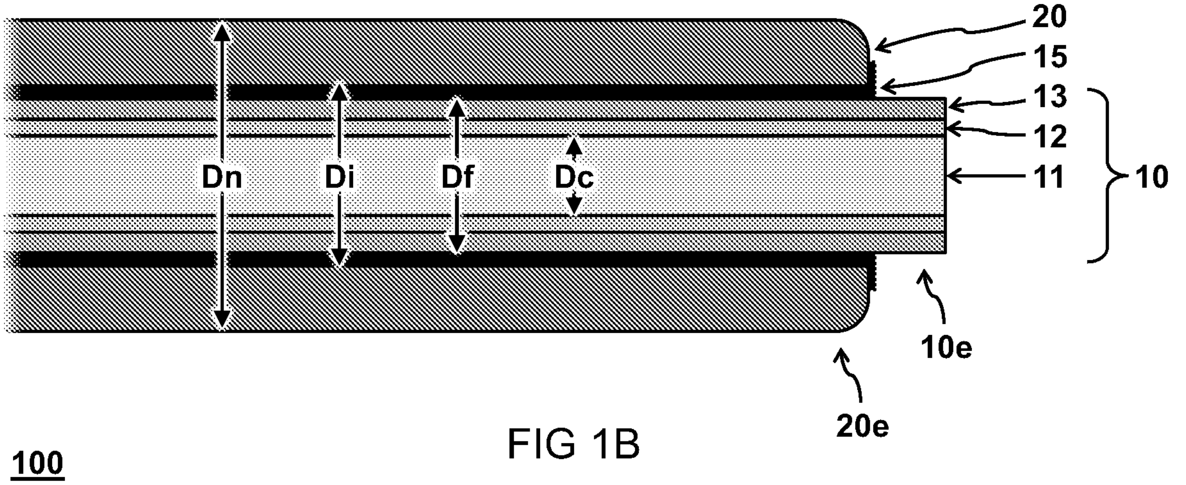
Figure 1C:
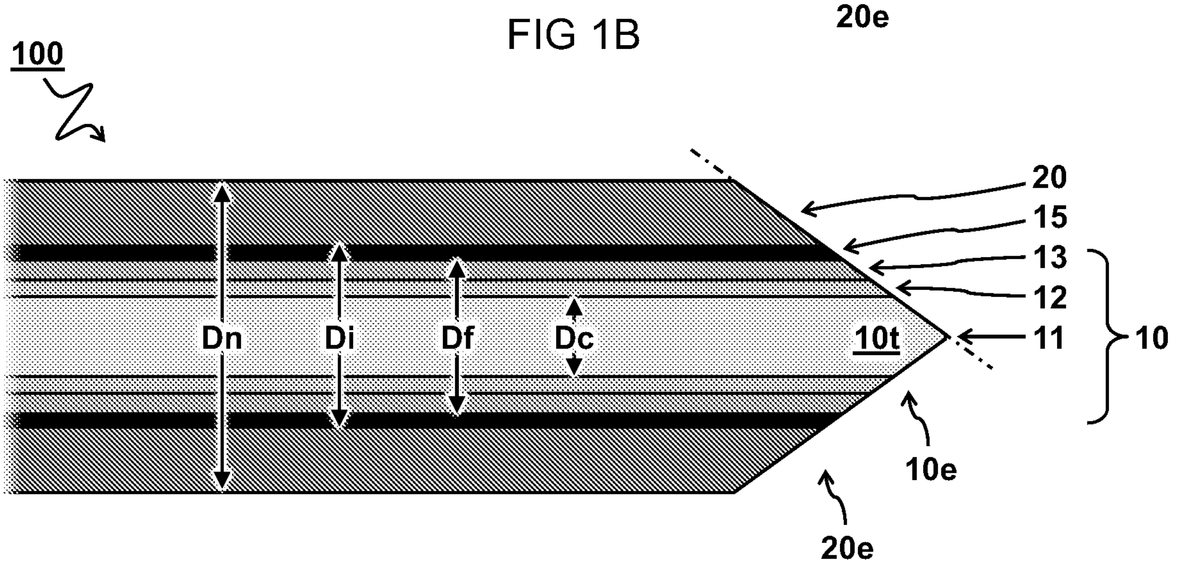

FIGS. 1A-1C illustrate manufacturing a fiber optic needle probe 100. Preferably, a fiber optic needle probe 100 comprises a length Ln of optical fiber 10 inside a hollow needle 20. For example, the hollow needle 20 is configured to supporting the optical fiber along the length. Most preferably, a distal end 10*e* of the optical fiber 10 is formed by a convex tip 10*t* protruding beyond a distal end 20*e* of the hollow needle 20.

By polishing, e.g., rubbing, the end of the optical fiber, a smooth, shiny, and/or clean surface can be achieved. In the present context, a very smooth or otherwise formed surface has the advantage of minimizing a tendency of fouling material to stick to the surface. For example, the smoothened tip has an average or maximum roughness "Ra" or "Ra max" less than ten micrometers, preferably less than five micrometers, most preferably less than one micrometer, less than half a micrometer, or even ≤0.1 μm. The smoother the surface, the less likely the fouling material sticks to the surface.

In some embodiments, the optical fiber 10 is fixated inside the hollow needle 20, e.g., by an adhesive layer 15 therebetween. By fixating the optical fiber 10, it can be prevented that the fiber is pushed back into the hollow needle 20. In this way, an exact position of the convex tip 10*t* with respect to the needle can be maintained. Preferably, the optical fiber 10 is fixated prior to the forming, e.g. polishing. of the distal end 10*e* of the optical fiber 10. By fixating the fiber before polishing, it can be easier to polish the fiber without the fiber bending, e.g., together with the hollow needle 20. Alternatively, the fiber can be formed independent of the needle, e.g., inserted after polishing or other processing. Most preferably, the distal end 10*e* of the optical fiber 10 is polished together with the distal end 20*e* of the hollow needle 20 to form the combined distal ends 10*e*,20*e* of the optical fiber 10 and hollow needle 20 into a continuous convex tip of the fiber optic needle probe 100. By providing a continuous convex tip, i.e., flush surface between the interfaces of the distal ends 10*e*,20*e* of the optical fiber 10 and hollow needle 20, the buildup of fouling at the border can be further alleviated. Preferably, the hollow needle 20 is formed, e.g. by polishing. to have a similar or the same surface roughness as the optical fiber 10. In this way, the fouling material can more easily slide further over the continuous flush and smooth surface, so it is further out of view for light exiting and entering the optical fiber 10.

In some embodiments, the hollow needle 20 is configured to hold a single optical fiber 10 inside, i.e., at most one. Preferably, the (or at least one) optical fiber 10 is centrally disposed inside the hollow needle 20. By arranging the optical fiber 10 at the center of the needle, it can be easier to polish the tip to protrude from the distal end of the needle 20. For example, the tip can be polished by contacting a polishing surface at an angle while rotating the probe along its central axis. Most preferably, the convex tip 10*t* of the optical fiber 10 protrudes along a line concentric with a circumference of the hollow needle 20. By providing the tip as close as possible to the central axis of the needle, e.g., within ten percent of the needle diameter, a symmetric arrangement can be obtained.

In some embodiments, the optical fiber 10 comprises a core 11, and a cladding 12 surrounding the core 11. Typically, the cladding has a lower index of refraction than the core. Accordingly, light traveling in the core can reflect from the core-cladding boundary due to total internal reflection. Preferably, the convex tip 10*t* of the optical fiber 10 is formed by a convex tip of the core 11 protruding beyond the surrounding cladding 12 at the distal end 10*e* of the optical fiber 10. In one embodiment, the optical fiber 10 comprises a coating 13 surrounding the cladding 12. The coating may provide further protection to the optical fiber and is typically made of a bendable material allowing some flexibility to the fiber. Preferably, coating 13 is of a polishable material, e.g. a metal such as aluminum. For example, a metal coating may provide a smoother and/or more durable surface when polished compared to a plastic/polymer coating. Most preferably, the cladding 12 protrudes beyond the surrounding coating 13 at the distal end 10*e* of the optical fiber 10.

As described herein, the optical fiber is preferably comprised of a fused silica core surrounded by a fused silica cladding, surrounded by a coating layer. The refractive index of fused silica is about 1.45. This advantageously matches the refractive index of soft biological tissue, which is typically between about 1.40 and 1.45. By matching the refractive index of the fiber to that of tissue, little refraction of light occurs at the fiber-tissue interface. Accordingly, the fiber tip shape, which is in contact with the tissue to be analyzed, can have a minimal effect on the illumination of tissue by the light guided through the optical fiber and a minimal effect on the tissue volume from which the light is collected and guided back through the optical fiber to an analysis unit. Also, other materials can be used for the core and/or cladding.

In some embodiments, the distal end 10*e* of the optical fiber 10, including each of the core 11, cladding 12, and coating 13, is formed together into a continuous convex tip of the optical fiber 10, e.g. by polishing or other otherwise processing each of these layers together. For example, this may prevent fouling material from getting stuck between the distal end interfaces of the cladding 12 and coating 13. This continuous convex tip may also form a flush surface with the distal end of the surrounding needle 20 and the adhesive layer 15 there between. For example, the optical fiber 10 is adhered to an inside of the hollow needle 20 via a layer of glue and/or epoxy. Preferably, the adhesive material is relatively hard when it is cured. For example, a hardened adhesive such as epoxy can be particularly suitable to form a smooth continuous surface between ends 10*e*,20*e* of the optical fiber 10 and surrounding needle 20.

In some preferred embodiments, the optical fiber 10 is bendable, e.g., allowing a minimum bend radius between five and thirty times an outer diameter "Df" of its coating 13 (without breaking and/or losing essential functionality), preferably between ten and twenty times the outer diameter. In one embodiment, an outer diameter "Df" of the optical fiber 10 (e.g., including the outer coating 13) is between 10-500 μm, preferably between 100-300 μm. In another or further embodiment, the core 11 and/or cladding 12 of the optical fiber 10 has a diameter between 60-250 μm, most preferably between 80-150 μm. On the one hand, the core and/or cladding diameter in these ranges is found to be sufficiently large to allow a sufficiently large viewing window/surface at the convex tip 10*t*, which is not easily obscured, at least not completely, by fouling tissue remnants. On the other hand, the diameter is sufficiently small to still allow easy puncturing of tissue with minimal deformation. Also, a reasonable size tip can be formed essentially consisting of the light-guiding material.

In other or further preferred embodiments, the hollow needle 20 is relatively rigid, at least compared to the optical fiber 10. For example, this can be quantified by the bending stiffness or flexural rigidity of the hollow needle being higher than that of optical fiber 10 by at least a factor five, ten, twenty, fifty, hundred, or more. Preferably, the hollow needle 20 provides sufficient support to guide the optical fiber 10 to a designated position with minimal bending. For example, this can be quantified as the tip of the needle bending less than one millimeter off its central axis when a force of one Newton is applied at the distal end of the needle in a direction transverse to its length (while the needle is held at its proximal end).

In some embodiments, the hollow needle 20 is formed by a metal tube. Advantageously, a metal needle can be relatively thin yet rigid. Also, metal is found particularly suitable for polishing together with optical fiber 10. For example, the needle or tube essentially consists of stainless steel, preferably medical grade stainless steel such as AIS1316L stainless steel. Alternatively also other, preferably hard, materials can be used to form the hollow needle 20. Preferably, the material of the needle is at least suitable for polishing or other processing to smoothen a respective surface. In one embodiment, the hollow needle 20 has an outer diameter "Dn" less than one millimeter, preferably less than half a millimeter, e.g., 0.1-0.3 mm. In another or further embodiment, the hollow needle 20 has an inner diameter "Di" similar to the outer diameter "Df" of the optical fiber 10, preferably slightly larger by a factor between 1.01 (one percent) and 1.4 (forty percent), more preferably between 1.05 (five percent) and 1.2 (twenty percent), and most preferably between 1.08 (eight percent) and 1.12 (twelve percent). This may allow the optical fiber 10 to be inserted into the hollow needle 20 without requiring much adhesive material and keeping the overall diameter of the needle to a minimum. For example, the outer diameter "Dn" of the hollow needle 20 is larger than the outer diameter "Df" of the optical fiber 10 by at most a factor of two or three.

FIGS. 2A-2D illustrate variations of a fiber optic needle probe 100. In a preferred embodiment, the distal end of the optical fiber 10 is formed by a conical tip. By forming the tip in a conical or near-conical shape, the light-emitting interface can be (near) rotation symmetric while still providing a sharp end to penetrate tissue. In this way, light can be emitted and received without preferential direction, at least at a circumferential angle, and the measurement is not affected by this angle. Furthermore, the tendency of fouling tissue sticking to a conical tip can be reduced, e.g., due to the additional (circumferential) curvature of the tip. Alternatively, also other tip shapes for the optical fiber 10 can be envisaged, such as a beveled distal end surface or double beveled (V-shaped) distal end surface, e.g., wherein the distal end of the optical fiber protrudes beyond the distal end of the hollow needle to at least allow fouling tissue to easily slide beyond the edge of the optical input/output.

Figure 2A:
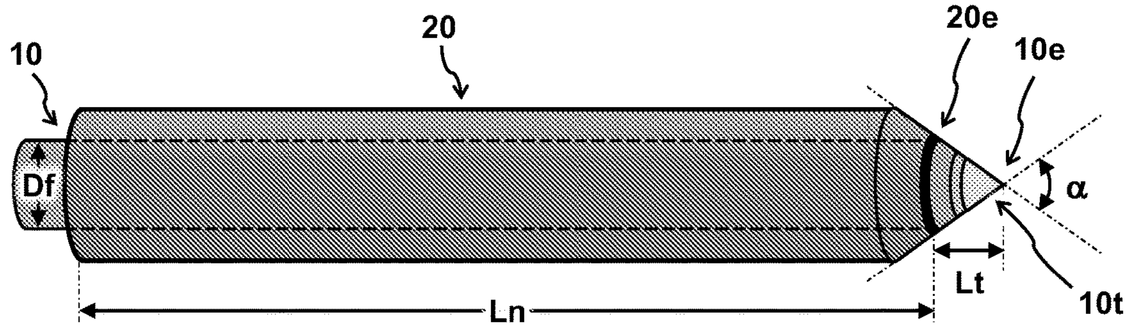
FIGS. 2A-2D illustrate variations of a fiber optic needle probe.

In some embodiments, e.g., as shown in FIG. 2A, the combined distal ends 10*e*,20*e* of the optical fiber 10 and hollow needle 20 are formed into a continuous conical tip of the fiber optic needle probe 100. For example, the distal end 10*e* end of the optical fiber 10 has a conically converging, circumferentially round shape ending in a relatively sharp apex. Preferably, the convex tip 10*t* at the distal end 10*e* of the optical fiber 10 protrudes beyond the distal end 20*e* of the hollow needle 20 at least by a distance corresponding to length "Lt" of the tip 10*t*. For example, the length "Lt" of the tip 10*t* disposed at the distal end 10*e* of the optical fiber 10 is at least fifty micrometers, preferably at least one hundred fifty or at least two hundred micrometers. For example, the length "Lt" of the fiber optic tip 10*t* is determined by the diameter "Df" of the optical fiber 10 and the apex angle $\alpha$, e.g. cone angle, with which the distal end 10*e* of the fiber is formed. For example, the length of a cone can be calculated as $Lt=(Df/2)/\tan(\alpha/2)$.

Figure 2B:
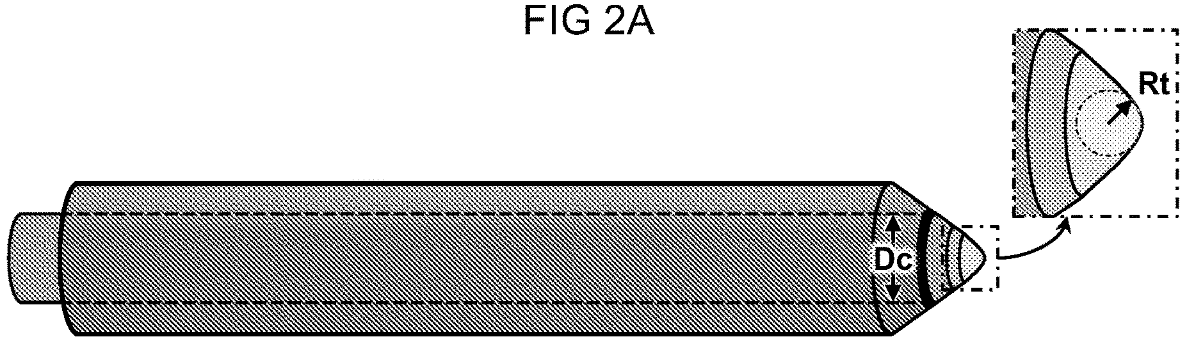

In other or further embodiments, e.g., as shown in FIG. 2B, some rounding the tip apex can be acceptable. Preferably at least, the tip apex has a maximum radius of curvature Rt less than an outer radius of the optical fiber, e.g., by at least a factor two, three, five, ten, twenty, fifty, hundred, or more. For example, the maximum radius of curvature Rt of the tip apex is less than one hundred micrometers, less than fifty micrometers, or less than ten micrometers. The smaller the tip apex radius, the sharper the tip and the easier it may be to penetrate tissue without compressing the tissue (which is important, e.g., in measuring a resection margin).

Figure 2C:
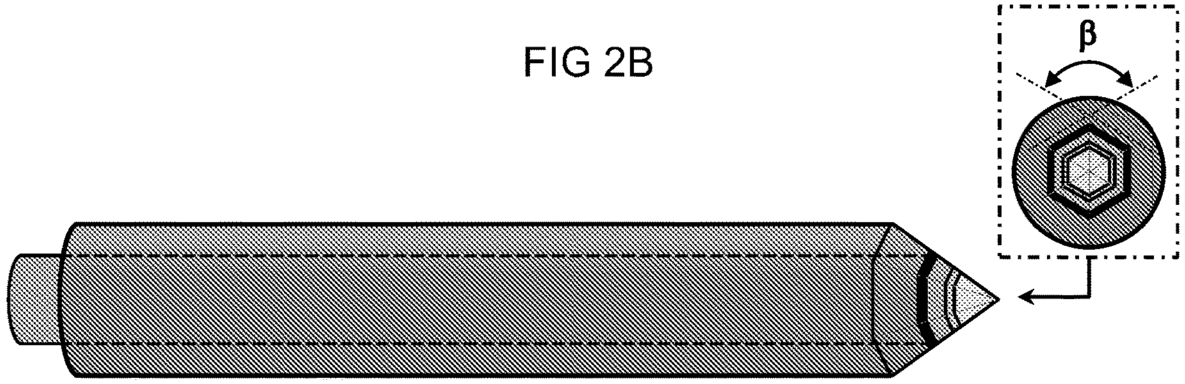

In other or further embodiments, e.g., as shown in FIG. 2C, deviation from a circumferentially round shape tip can be acceptable. For example, the tip can be faceted, as shown. Preferably at least an azimuth or circumferential angle $\beta$, as indicated, is relatively large, e.g., at least sixty degrees (corresponding to at least three facets), at least ninety degrees (corresponding to at least four facets), at least hundred twenty degrees (corresponding to at least six facets), or as close as possible to hundred eighty degrees (corresponding to a smooth circle). The rounder the circumferential shape, the fewer edges it has, and the less a tendency of fouling tissue sticking to edges.

Figure 2D:
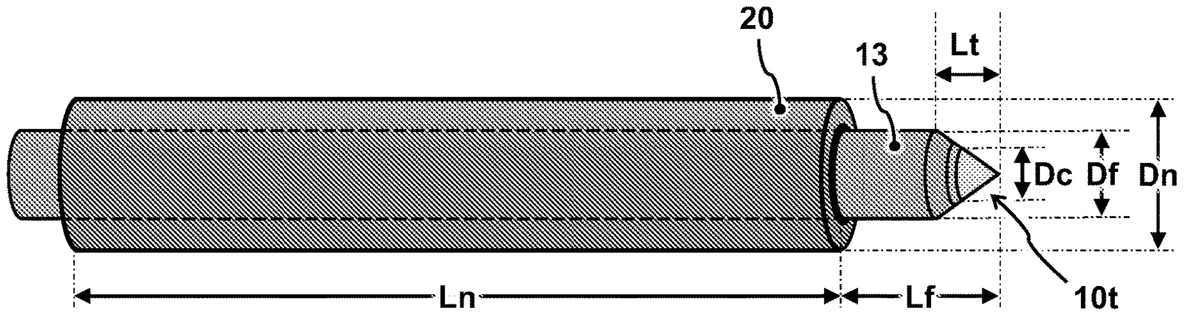

In other or further embodiments, e.g., as shown in FIG. 2D, there can be a discontinuity between the distal ends of the optical fiber 10 and hollow needle 20. For example, the tip of the optical fiber 10 can be formed before inserting the optical fiber 10 into the hollow needle 20. In one embodiment, a length "Lf" of the optical fiber 10 may protrude beyond the distal end of the hollow needle 20. For example, the protruding length of the optical fiber may have at least some stiffness to resist bending when the convex tip 10*t* is inserted into a tissue, in particular when part of the length "Ln" is supported inside the hollow needle 20. Preferably, the length "Lf" by which (the apex of) the optical fiber 10 protrudes from the hollow needle 20 is less than two centimeters, less than one centimeter, most preferably equal or close to the length "Lt" of the tip 10*t*.

Figure 3:
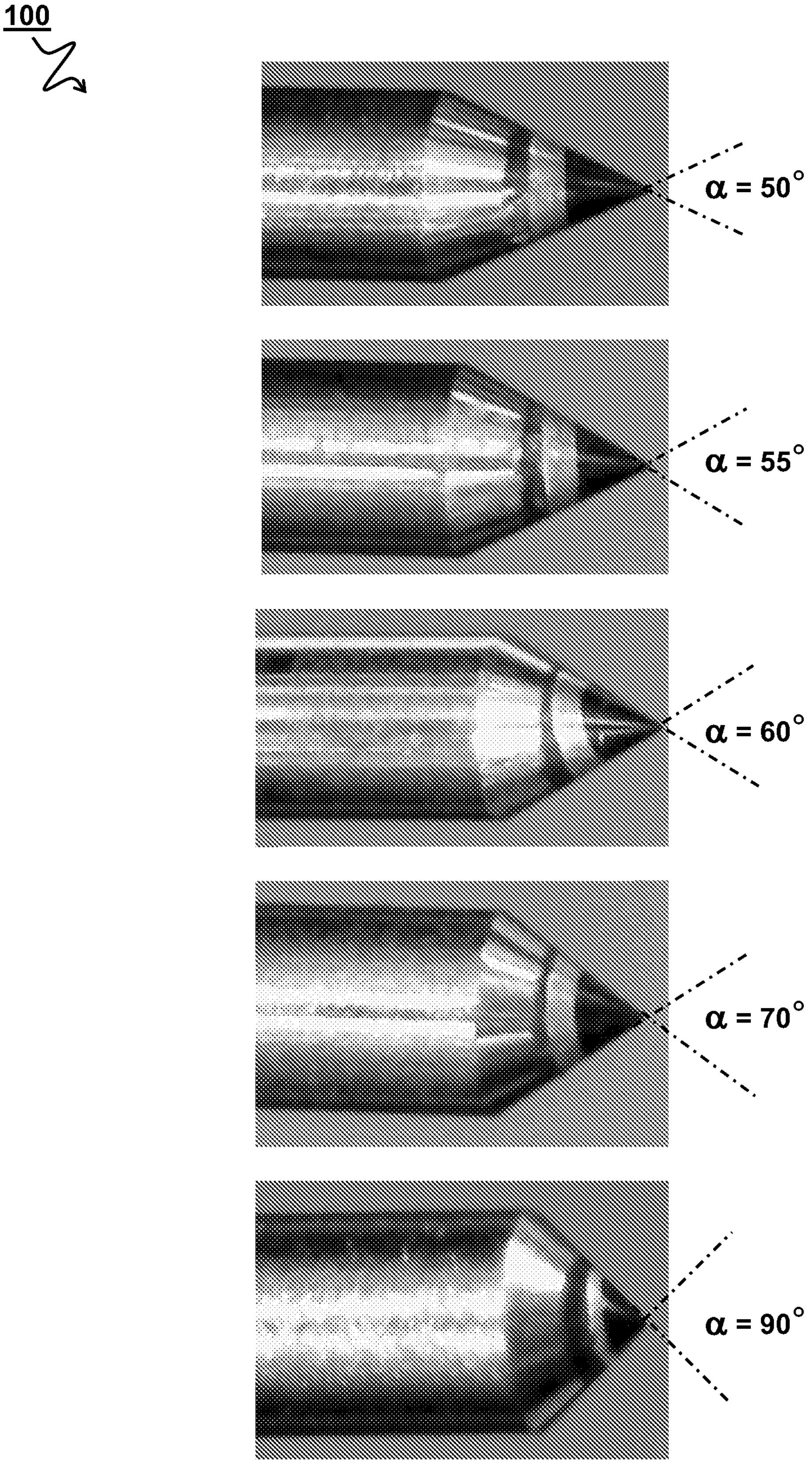
FIG. 3 illustrates photographs of fiber optic needle probes manufactured as described herein with various cone angles.

FIG. 3 illustrates photographs of fiber optic needle probes 100 manufactured as described herein with various cone angles "$\alpha$". Preferably, the tip has a relatively sharp apex angle $\alpha$ (e.g. cone angle), e.g. less than hundred degrees (plane angle), preferably less than ninety degrees, most preferably less than seventy degrees. The relatively sharp tip can help to clear fouling off the tip. On the other hand, making the tip too sharp can increase the chance of breaking. So preferably, the apex angle is at least thirty degrees, preferably at least forty degrees, e.g. between fifty and ninety degrees.

In the embodiments shown, the probes comprise an optical fiber with a core and cladding of fused silica. The core has a diameter of 105 micrometers, and the cladding has a diameter of 125 micrometers. Around the core and cladding, the optical fiber has a coating of aluminum with an outer diameter of 175 micrometers. The optical fiber is glued inside a metal tube having an inner diameter between 180-200 micrometers and an outer diameter of 300 micrometers.

Figure 4:
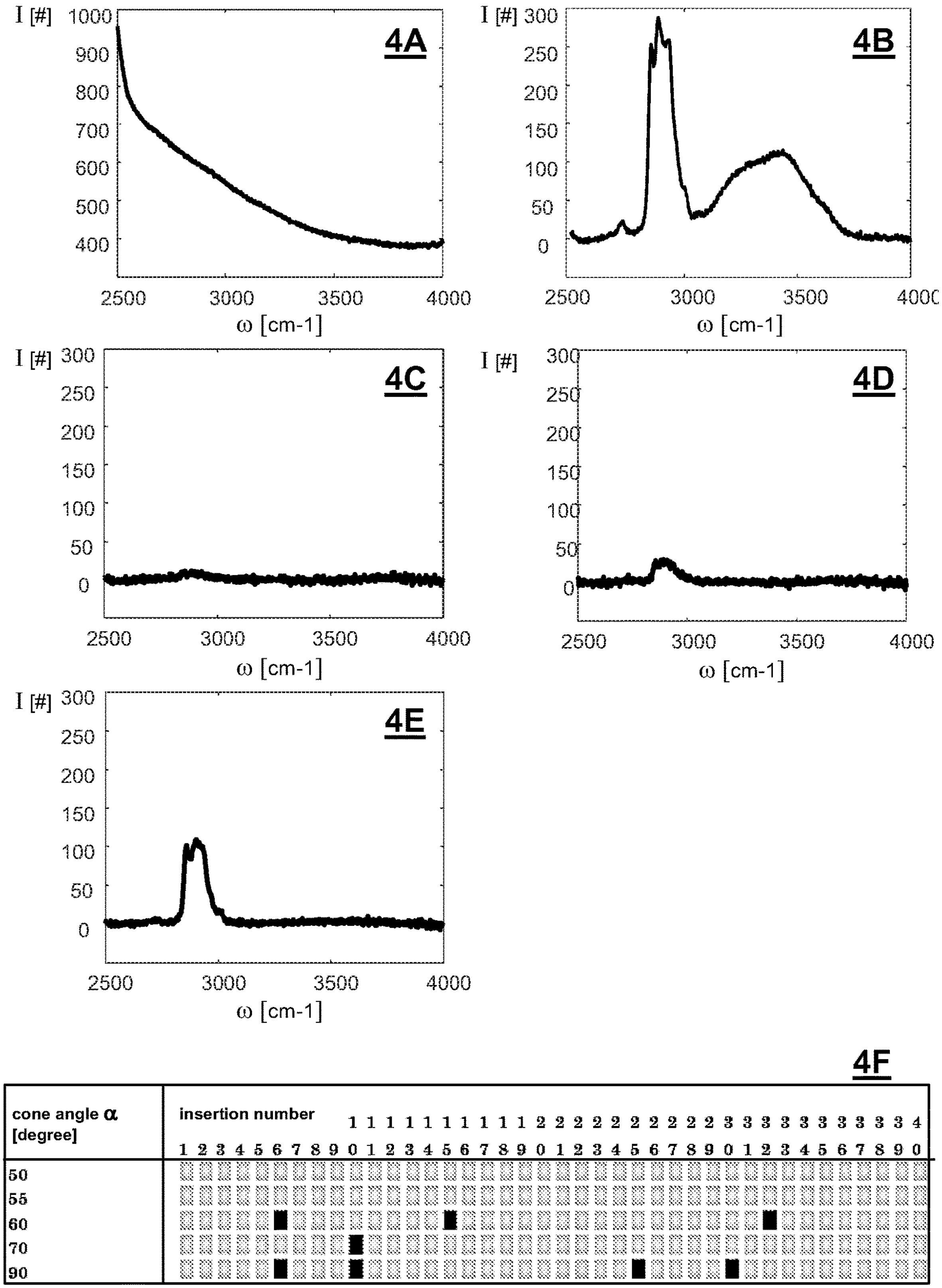
FIG. 4 illustrates measurements to determine a tendency of tissue sticking on the various fiber optic needle probes.

FIG. 4 illustrates measurements to determine a tendency of tissue sticking on the various fiber optic needle probes.

Graph 4A illustrates a spectrum obtained with a fiber optic needle probe having a 90 degrees conical tip held in air before first use, showing a background signal generated in the fiber-optic needle itself.

Graph 4B illustrates a Raman spectrum obtained with the same probe, now inserted in tissue after subtraction of the background signal, showing tissue signal contributions in the CH-stretching region and OH-stretching region.

Graph 4C illustrates a Raman spectrum obtained with the same probe in air, after retraction from tissue after subtraction the background signal, showing virtually no residual tissue signal due to contamination Graph 4D illustrates a Raman spectrum obtained with the same probe in air, after retraction from tissue after subtraction the background signal, showing a weak residual tissue signal due to contamination of the tip Graph 4E illustrates a Raman spectrum obtained with another fiber optic needle in air, this time having a 3-facet beveled tip, after retraction from tissue after subtraction of the background signal, showing a relatively strong residual tissue signal due to contamination of the tip. Comparing graphs 4D and 4E, it will be appreciated that even if there is some residual tissue, the interference thereof will be minimal for a conical-shaped tip compared to a faceted tip.

Table 4F illustrates experiments of contamination rate of fiber optic needle probes with a conical tip in a range of conical angles (50-90 degrees full angle). Each fiber optic needle was inserted in and retracted from fresh calf tongue tissue. This insertion and extraction were repeated 40× times for each fiber-optic needle. The insertion and extraction speeds were 3.7 mm/second. Insertion depth into the tissue was 10 mm. During the needle insertions into the tongue tissue, Raman spectra of the tissue were measured along the needle insertion path, with a 100 ms/spectrum signal collection time. After each retraction of the needle from the tissue, Raman spectra were measured with the fiber-optic needle tip in the air with a 100 ms/spectrum signal collection time. After each fifth insertion, or if tissue contamination was suspected after a retraction, the needle tip was inspected for any visible signs of mechanical deterioration or tissue contamination and photographed. In all cases, the contamination rate was found to be 10%. In all cases, the fiber optic needle said contamination was removed by the next insertion into the tissue. This demonstrates that the conical tip is particularly advantageous for applications wherein a fiber optic needle probe 100 needs to be repeatedly inserted into a tissue, such as for determining a resection margin.

Figure 5:
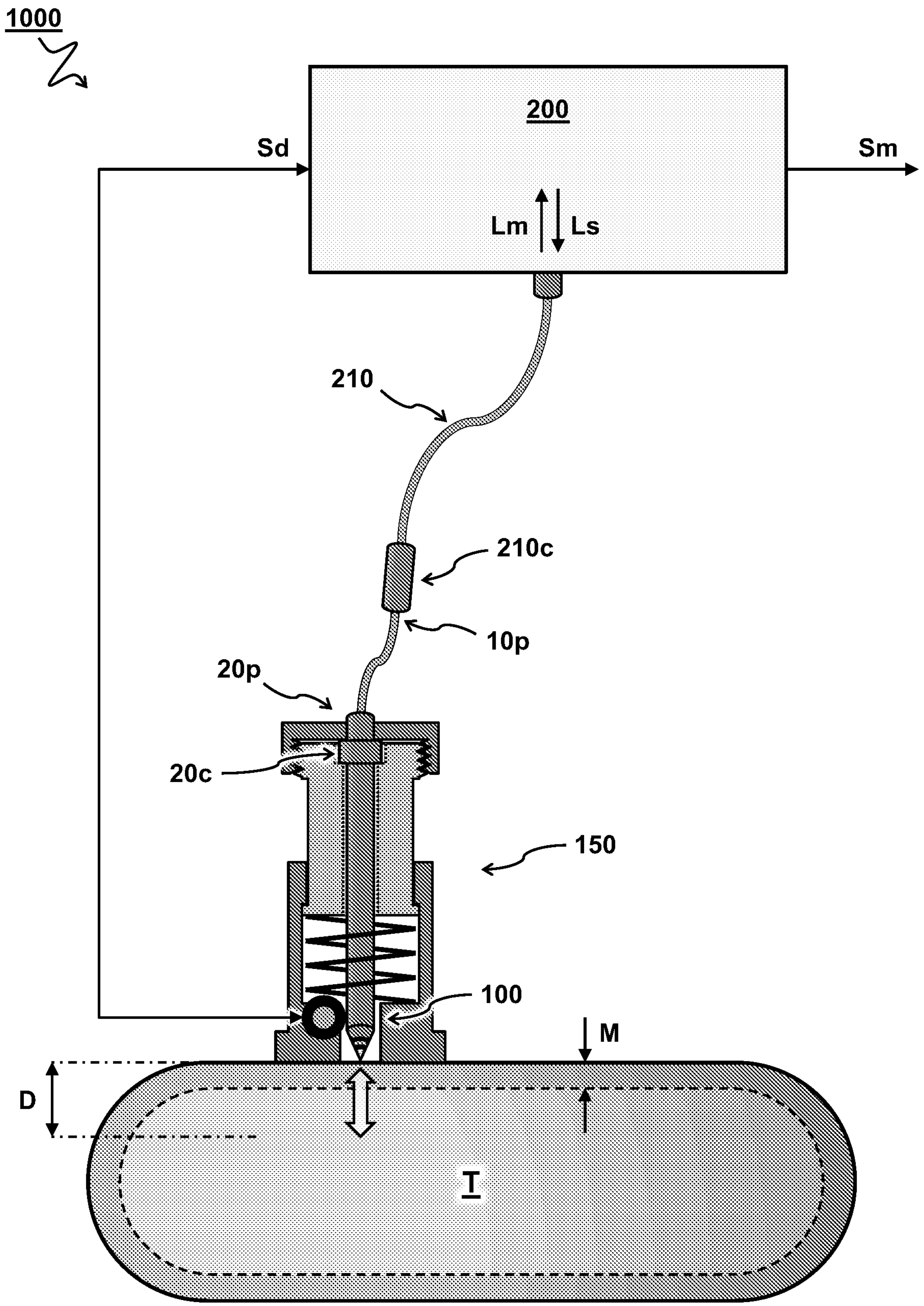
FIG. 5 illustrates an apparatus and measurement system comprising the fiber optic needle probe.

FIG. 5 illustrates an apparatus 150 and measurement system 1000 comprising the fiber optic needle probe 100.

In some embodiments, the fiber optic needle probe 100 as described herein is comprised in or couples to an apparatus 150 for measuring a tissue "T". For example, the tip 10*t* at the distal end 10*e* of the optical fiber 10 is configured for insertion/injection into the tissue "T". In one embodiment, the apparatus 150 comprises a housing with a tissue engaging surface. In another or further embodiment, the housing comprises a needle guiding structure configured to guide the fiber optic needle probe. Preferably, the structure is configured to guide the needle transverse, e.g. perpendicular, to the tissue engaging surface. Most preferably, the apparatus is configured for repeated insertion of the tip 10*t* of the fiber optic needle probe 100 into the tissue "T". For example, the needle guiding structure is fixedly arranged in the housing normal to a reference plane formed by the tissue engaging surface, to guide the needle perpendicular to the tissue engaging surface.

In some embodiments, the housing comprises at least one of an actuator or a sensor configured to receive or generate a depth signal Sd to determine a depth position D of the tip 10*t* relative to a tissue engaging surface. For example, the apparatus can be used to measure a resected tissue specimen which is cut along a tissue resection surface. For example, the measurement comprising ex-vivo determining a resection margin of healthy tissue surrounding tumour tissue based on the spectral measurements as a function of the depth position of the needle tip relative to the tissue resection surface.

In a preferred embodiment, the fiber optic needle probe 100 is exchangeable from the housing of the apparatus 150. In one embodiment, the hollow needle 20 comprises a connection structure 20*c* configured to fixate the fiber optic needle probe 100 to a moveable part of the housing which moveable part is configured to move the fiber optic needle probe 100 with respect to the tissue engaging surface into the tissue "T". For example, the hollow needle 20 comprises a thickened section at or near a proximal end 20*p* of the needle which section can be clamped by the moveable part of the housing to fixate an axial coordinate of the needle. Preferably, the axial coordinate is predetermined so the position of the tip with respect to the tissue engaging surface is precisely known.

In some embodiments, the fiber optic needle probe 100 and/or apparatus 150 as described herein are comprised in, or couple to, a measurement system 1000 for measuring a tissue "T", e.g. by means of an optical device 200. In one embodiment, the optical device 200 is configured to transmit source light "Ls" into a proximal end 10*p* of the optical fiber 10. For example, the optical device comprises or couples to a light source (not shown) configured to generate the source light "Ls". In another or further embodiment, the optical device 200 is configured to receive measurement light "Lm" from the proximal end 10*p* resulting from the source light "Ls" having interacted with the tissue "T" at the tip 10*t*. For example, the optical device comprises or couples to a sensor (not shown) configured to measure the measurement light "Lm". For example, the optical device 200 is configured to measure a Raman spectrum of the tissue "T".

In some embodiments, the tissue "T" is a resected tissue specimen. For example, the system 1000 is configured to measure a margin "M" of healthy tissue surrounding tumor tissue. In one embodiment, the system is configured to measure spectral signatures of the tissue as a function of a depth "D" of the tip of the probe below the tissue surface. For example, one or more spectral signatures, such as Raman, Fluorescence, Diffuse Reflection (Scattering), and/or Absorption spectra, can be used to distinguish healthy tissue from tumor tissue. For example, the depth is determined by a sensor or actuator with respect to the tissue engaging surface of the apparatus. For example, the apparatus is configured to receive or output a set of depth signals Sd, receive a set of spectra corresponding to the set of depth signals, and determine a signal Sm indicative of a margin "M" of healthy tissue surrounding tumor tissue based on the depth-dependent spectra. The fiber optic needle probe 100 is preferably configured as an exchangeable part of the system 1000. For example, the fiber optic needle probe 100 can be inserted into the apparatus 150, and the proximal end 10*p* of the optical fiber 10 can be connected to the optical device 200, e.g. via optical connector 210*c* and further optical fiber 210, as shown. Also, other connections can be provided, e.g. electrical or wireless connections for transmitting the depth signal Sd.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise.

The invention claimed is:

1. A fiber optic needle probe comprising a hollow needle having a lumen, the hollow needle supporting a single optical fiber inserted inside the lumen along a length of the single optical fiber so that the single optical fiber is centrally disposed inside the hollow needle, wherein a flexural rigidity of the hollow needle is higher than that of the single optical fiber by at least a factor ten, wherein a distal end of the single optical fiber is formed by a convex tip protruding beyond a distal end of the hollow needle, wherein the distal end of the single optical fiber is formed by a conical tip having a cone angle less than one hundred degrees, wherein the distal end of the single optical fiber is polished together with the distal end of the hollow needle to form combined distal ends of the single optical fiber and hollow needle into a continuous convex tip of the fiber optic needle probe, and wherein the continuous convex tip forms a flush surface between respective interfaces of the distal end of the optical fiber and the distal end of the hollow needle.

2. A fiber optic needle probe comprising a hollow needle having a lumen, the hollow needle supporting a single optical fiber inserted inside the lumen along a length of the single optical fiber so that the single optical fiber is centrally disposed inside the hollow needle, wherein a flexural rigidity of the hollow needle is higher than that of the single optical fiber by at least a factor ten, wherein the single optical fiber is fixated inside the hollow needle by an adhesive layer therebetween, wherein a distal end of the single optical fiber is formed by a convex tip protruding beyond a distal end of the hollow needle, wherein the distal end of the single optical fiber is polished together with the distal end of the hollow needle to form combined distal ends of the single optical fiber and hollow needle into a continuous convex tip of the fiber optic needle probe, wherein the continuous convex tip forms a flush surface between respective interfaces of the distal end of the optical fiber and the distal end of the hollow needle.

3. The fiber optic needle probe according to claim 2, wherein the single optical fiber is fixated prior to the forming of the distal end of the single optical fiber.

4. A fiber optic needle probe comprising a hollow needle having a lumen, the hollow needle supporting a single optical fiber inserted inside the lumen along a length of the single optical fiber so that the single optical fiber is centrally disposed inside the hollow needle, wherein a flexural rigidity of the hollow needle is higher than that of the single optical fiber by at least a factor ten, wherein the single optical fiber comprises a core and a cladding surrounding the core, wherein a distal end of the single optical fiber is formed by a convex tip protruding beyond a distal end of the hollow needle, wherein the convex tip of the single optical fiber is formed by a convex tip of the core protruding beyond the cladding at the distal end of the single optical fiber, wherein the distal end of the single optical fiber is polished together with the distal end of the hollow needle to form combined distal ends of the single optical fiber and hollow needle into a continuous convex tip of the fiber optic needle probe, and wherein the continuous convex tip forms a flush surface between respective interfaces of the distal end of the optical fiber and the distal end of the hollow needle.

5. A fiber optic needle probe comprising a hollow needle supporting a single optical fiber along a length of the single optical fiber that is centrally disposed inside the hollow needle, wherein the single optical fiber comprises a core, a cladding surrounding the core, and a coating surrounding the cladding, wherein a distal end of the single optical fiber is formed by a convex tip protruding beyond a distal end of the hollow needle, wherein the cladding protrudes beyond the coating surrounding the cladding at the distal end of the single optical fiber, wherein the distal end of the single optical fiber including each of the core, cladding, and coating is formed together with the distal end of the hollow needle to form combined distal ends of the single optical fiber and hollow needle into a continuous convex tip of the fiber optic needle probe, and wherein the continuous convex tip forms a flush surface between respective interfaces of the distal end of the optical fiber and the distal end of the hollow needle.

6. The fiber optic needle probe according to claim 5, wherein the single optical fiber is bendable, allowing a minimum bend radius between ten and twenty times an outer diameter of the single optical fiber, wherein the hollow needle is relatively rigid compared to the single optical fiber, and wherein a flexural rigidity of the hollow needle is higher than that of the single optical fiber by at least a factor ten.

7. The fiber optic needle probe according to claim 1, wherein the hollow needle is formed by a metal tube having an outer diameter less than one millimeter and an inner diameter larger than an outer diameter of an outer protective coating of the single optical fiber.

8. The fiber optic needle probe according to claim 1, wherein the fiber optic needle probe is included in an apparatus for measuring a tissue, wherein the apparatus comprises:

a housing comprising a tissue engaging surface and a needle guiding structure configured to guide the fiber optic needle probe transverse to the tissue engaging surface for repeated insertion of the tip of the fiber optic needle probe into the tissue at different locations to reach a respective depth position below the tissue surface, wherein the housing comprises at least one device taken from the group consisting of:

an actuator, and a sensor;

wherein the at least one device is configured to receive or generate a depth signal to determine a depth position of the convex tip relative to the tissue engaging surface.

9. The fiber optic needle probe according to claim 8, configured to be exchangeable from the housing of the apparatus.

10. The fiber optic needle probe according to claim 8, wherein the hollow needle comprises a connection structure configured to fixate the fiber optic needle probe to a moveable part of the housing which moveable part is configured to move the fiber optic needle probe with respect to the tissue engaging surface into the tissue.

11. The fiber optic needle probe according to claim 1, further comprising:

an optical device configured to perform:

transmitting source light into a proximal end of the single optical fiber, and receiving measurement light from the proximal end resulting from the source light having interacted with the tissue at the tip.

12. The fiber optic needle probe according to claim 1, wherein the distal end of the optical fiber has a same surface roughness as the distal end of the hollow needle.

13. The fiber optic needle probe according to claim 5, wherein the coating is a metal coating.

* * * * *